US012569411B2

(12) United States Patent　　(10) Patent No.:　US 12,569,411 B2
Cölfen et al.　　　　　　　　　　(45) Date of Patent:　　Mar. 10, 2026

(54) PREPARATION AND FULLY COMPOUNDED STOCK FOR USE IN MEDICAL OR DENTAL APPLICATIONS, MEDICAL OR DENTAL PRODUCT AND USE AND PREPARATION THEREOF

(71) Applicant: GEBR. BRASSELER GMBH & CO. KG, Lemgo (DE)

(72) Inventors: Helmut Cölfen, Constance (DE); Elena Sturm, Constance (DE); Julian Konsek, Constance (DE); Michael Küllmer, Lemgo (DE)

(73) Assignee: GEBR. BRASSELER GMBH & CO. KG, Lemgo (DE)

( * ) Notice: Subject to any disclaimer, the term of this patent is extended or adjusted under 35 U.S.C. 154(b) by 1080 days.

(21) Appl. No.: 17/630,711

(22) PCT Filed: Jul. 27, 2020

(86) PCT No.: PCT/EP2020/071127

§ 371 (c)(1),
(2) Date: Jan. 27, 2022

(87) PCT Pub. No.: WO2021/023547

PCT Pub. Date: Feb. 11, 2021

(65) Prior Publication Data

US 2022/0265519 A1　　Aug. 25, 2022

(30) Foreign Application Priority Data

Aug. 6, 2019　(DE) .......................... 102019211781.3

(51) Int. Cl.
A61K 6/35　　　　(2020.01)
A61K 6/60　　　　(2020.01)
(Continued)

(52) U.S. Cl.
CPC ................ A61K 6/864 (2020.01); A61K 6/60 (2020.01); A61K 6/78 (2020.01); A61K 6/853 (2020.01);
(Continued)

(58) Field of Classification Search
None
See application file for complete search history.

(56) References Cited

U.S. PATENT DOCUMENTS 4,319,927 A　*　3/1982　Segal ...................... C04B 7/421
106/734
2006/0292350 A1　12/2006　Kawamura et al.
(Continued)

FOREIGN PATENT DOCUMENTS

CN　　102432680 A　*　5/2012
CN　　104043149 A　　9/2014
(Continued)

OTHER PUBLICATIONS

CN-102432680-A, English translation (Year: 2012).*
(Continued)

*Primary Examiner* — Stefanie J Cohen
(74) *Attorney, Agent, or Firm* — SHUTTLEWORTH & INGERSOLL, PLC; Timothy J. Klima

(57) ABSTRACT

According to the invention, a preparation is described which contains at least one calcium compound selected from the group consisting of calcium phosphates, calcium fluorides and calcium fluorophosphates and hydroxyl derivatives and carbonate derivatives of these calcium salts, calcium hydroxides and calcium oxides precipitated using at least one protein component selected from proteins and protein hydrolysates, and at least one crosslinking agent for the protein component and/or non-set cement.

17 Claims, 2 Drawing Sheets

(51) Int. Cl.

| | |
|---|---|
| *A61K 6/78* | (2020.01) |
| *A61K 6/853* | (2020.01) |
| *A61K 6/864* | (2020.01) |
| *C04B 12/02* | (2006.01) |
| *C04B 14/28* | (2006.01) |
| *C04B 24/14* | (2006.01) |
| *C04B 28/02* | (2006.01) |
| *C04B 28/34* | (2006.01) |
| *C04B 103/00* | (2006.01) |
| *C04B 111/00* | (2006.01) |

(52) U.S. Cl.
CPC ............ *C04B 12/025* (2013.01); *C04B 14/28* (2013.01); *C04B 24/14* (2013.01); *C04B 28/02* (2013.01); *C04B 28/344* (2013.01); *C04B 2103/001* (2013.01); *C04B 2111/00836* (2013.01)

(56) References Cited

U.S. PATENT DOCUMENTS

| | | | |
|---|---|---|---|
| 2007/0134285 A1 | 6/2007 | Lynn et al. | |
| 2012/0115780 A1* | 5/2012 | Delaney | C04B 28/344 514/8.1 |
| 2012/0207839 A1 | 8/2012 | Liu et al. | |
| 2014/0312517 A1* | 10/2014 | Engqvist | C04B 28/344 264/19 |
| 2014/0314691 A1* | 10/2014 | Eckert | A61K 8/64 424/53 |
| 2019/0009428 A1* | 1/2019 | Dienemann | B28B 1/001 |
| 2020/0071596 A1* | 3/2020 | Al-Yami | C09K 8/473 |

FOREIGN PATENT DOCUMENTS

| | | | | |
|---|---|---|---|---|
| CN | 104623729 A | * | 5/2015 | |
| CN | 108164215 A | * | 6/2018 | C04B 18/027 |
| DE | 19812714 A1 | | 9/1999 | |
| DE | 19962090 A1 | | 6/2000 | |
| JP | H08117323 A | | 5/1996 | |
| JP | 2014098001 A | | 5/2014 | |

OTHER PUBLICATIONS

CN-104623729-A, English translation (Year: 2015).*

CN-108164215-A, English translation (Year: 2018).*

German Office Action dated Mar. 19, 2020 from counterpart German Patent Application No. 10 2019 211 781.3.

International Search Report and Written Opinion dated Oct. 19, 2020 from counterpart International Patent Application No. PCT/EP2020/071127.

Chang et al: "Preparation of a Porous Hydroxyapatite/Callogen Nanocomposite Using Gluteraldehyde as a Crosslinkage Agent", Journal Of Materials Science Letters, Chapman and Hall LTD. London, GB, Bd. 20, Nr. 13, Jul. 1, 2001 (Jul. 1, 2001), pp. 1199-1201, XP001 099925, ISSN: 0261-8028.

Kruppke Benjamin et al: "Biomaterial based treatment of osteoclastic/osteoblastic cell imbalance—Gelatin-modified calcium/strontium phosphates", Materials Science and Engineering C, Elsevier Science S.A, CH, Bd. 104, Jul. 3, 2019 (Jul. 3, 2019), XP085787209, ISSN: 0928-4931, DOI: 10.1 016/J.MSEC.2019.1 09933 [gefunden am Jul. 3, 2019].

Mai et al: "Histologie study of incorporation and resorption of a bone cement-collagen composite: an in vivo study in the minipig", Oral Surgery, Oral Medicine, Oral Pathology, Oral Radiology and Endodontics, Mosby-Year Book, St. Louis, MO, US, Bd. 105, Nr. 3, Feb. 14, 2008 (Feb. 14, 2008), Seiten e9-e14, XP022478587, ISSN: 1079-2104, DOI: 10.1 016/J.TRIPLE0.2007.09.016.

Yoon B-H et al. "Stability and cellular responses to fluorapatite-collagen composites" Biomaterials, Elsevier. Amsterdam, ND vol. 26, No. 16, Jun. 1, 2005 (Jun. 1, 2005), pp. 2957-2963, [retrieved on Jun. 1, 2005] DOI: 10.10 16/J.BIOMATERIALS.2004.07.062 ISSN: 0142-9612, XP025280610.

Korean Office Action dated Aug. 19, 2025 from counterpart Korean App No. 10-2022-7006139.

* cited by examiner

Härte der Kompositmaterialien in Abhängigkeit des Vernetzers

PREPARATION AND FULLY COMPOUNDED STOCK FOR USE IN MEDICAL OR DENTAL APPLICATIONS, MEDICAL OR DENTAL PRODUCT AND USE AND PREPARATION THEREOF

This application is the National Phase of International Application PCT/EP2020/071127 filed Jul. 27, 2020 which designated the U.S.

This application claims priority to German Patent Application No. 102019211781.3 filed Aug. 6, 2019, which application is incorporated by reference herein.

The present invention relates to a preparation and a ready-mix for use in medical or dental applications. In addition, the present invention relates to a medical or dental product, the use and production thereof.

Dental substitute materials or bone substitute materials used today, such as ceramics or polymeric materials, suffer from the disadvantage of not being biomimetic or bioinert. In other words, the composition and structure of conventional materials largely differ from the body's own materials such that use thereof creates problems in processing and long-term stability and biocompatibility of the tooth replacement materials or bone substitutes. Due to the different composition and structure of the conventional tooth substitute materials or bone materials compared to corresponding natural tooth and bone materials, problems may also arise due to different hardness of the materials. Often, the tooth substitute materials or bone substitute materials are thus subjected to greater stress, leading to high wear thereof.

Based on that state of the art, it is an object of the present invention to provide a preparation as well as a ready-mix for use in medical or dental applications that does not exhibit the above-mentioned problems, and thus consequently is biomimetic or bioinspired and is thus similar in composition and structure to the materials to be replaced. Furthermore, it is an object of the present invention to provide a medical or dental product having improved biomimetic composition, durability and processability, as well as improved mechanical properties. Improved mechanical properties can be understood especially as high compressive strength, which should be at least 50 MPa.

Furthermore, it is also an object of the invention to provide a use of the product as well as a method for production thereof.

This object will be solved by a preparation comprising at least one calcium compound precipitated using at least one protein component selected from the group consisting of proteins and protein hydrolysates, and at least one cross-linking agent for the protein component and/or non-set cement.

By precipitating the calcium compound selected from the group consisting of calcium phosphates, calcium fluorides and calcium fluorophosphates, and hydroxyl derivatives and carbonate derivatives of these calcium salts, calcium hydroxides and calcium oxides, using at least one protein component, a composite (a composite compound respectively) is obtained which is characterized by high stability and high chemical similarity to endogenous tooth and bone materials, as endogenous tooth and bone materials predominantly contain calcium phosphates, such as hydroxyapatite in the tooth, and protein compounds. Thus, the composite obtained by precipitation is already characterized by very good biomimetic properties.

According to the invention, the biomimetic or bioinspired properties and especially also the mechanical stability and bonding ability to endogenous tooth or bone materials are increased by the preparation containing at least one cross-linking agent for the protein component and/or non-set cement. By adding a crosslinking agent for the protein component, the structure of the composite can be additionally crosslinked after activation of the crosslinking agent. Another bond is formed between the binding partner "protein component" and the crosslinking agent. This can significantly increase mechanical as well as chemical and biological stability and thus also resistance to degradation by macrophages of the material obtained. Compressive strengths of at least 50 MPa were achieved for a dental product made from the preparation according to the invention. In comparison, a compressive strength of $62.2\pm23.8$ MPa for enamel and $193.7\pm30.6$ MPa for dentin is reported in literature. The compressive strength will be determined as indicated by the following standard: Dentistry—Zinc oxide-eugenol cements and eugenol-free zinc oxide cements (ISO 3107:2011); German version: EN ISO 3107:2011.

In addition, a hardness of 70 HV0.3 could also be obtained for a dental product produced from the preparation by crosslinking the protein component with a crosslinking agent, but without setting the cement; in comparison, values of $274.8\pm18.1$ are reported in literature for enamel and $65.6\pm3.9$ for dentin. Hardness measurement was performed according to Vickers HV0.3: see "Metallic materials—Vickers hardness test—Part 1: Test method (ISO 6507-1: 2018); German version EN ISO 6507-1:2018".

Use of non-set cement shows a similar effect on mechanical stability, however, the increase in mechanical stability will not be achieved by cross-linking the protein component, but by recrystallization of the calcium compound and the cement after activation of the cement using a suitable solvent, such as water. To prevent premature recrystallization and thus hardening of the preparation, the cement is added to the preparation in a non-set form. This means that the cement is not yet activated, but after having been activated, will be capable of recrystallization and thus restructurization and densification of the material by the properties described above.

Due to the compounds contained, which are nature-identical or at least close to nature in structure and composition, the preparation enables production of a medical or dental product having improved biocompatibility, workability with endogenous tooth or bone materials and very good long-term stability. In particular, due to its properties, the preparation according to the invention is particularly suitable for the production of a tooth substitute material, a bone substitute material, a root canal sealer, a root filling material, a retrograde filling material, a pulp capping material or a perforation closure material.

The subclaims include advantageous further embodiments of the invention.

According to an advantageous further embodiment, the non-set cement is selected from the group consisting of calcium silicate cement, calcium phosphate cement and mixtures thereof. Calcium silicate cements and calcium phosphate cements are characterized by having a high degree of structural similarity to endogenous tooth and bone materials. Calcium phosphate cements are also particularly preferred due to their further high chemical similarity to endogenous tooth and bone materials.

Further advantageously, the calcium compound is selected from the group consisting of $Ca(H_2PO_4)_2 \cdot xH_2O$, wherein x is an integer of from 0 to 6, $CaHPO_4 \cdot xH_2O$, wherein x is an integer of from 0 to 6, $Ca_8(HPO_4)_2$ $(PO_4)_4 \cdot 5H_2O$, $Ca_3(PO_4)_2$, $Ca_{10}(PO_4)_6(OH)_2$, $Ca_{10}(PO_4)_6F_2$, $(Ca_{10-a}M_a)[(PO_4)_{6-b}Y_b][(OH)_{2-c}X_c]$ wherein $M=Na^+$, $Sr^{2+}$, $Mg^{2+}$, $Ba^{2+}$, $Pb^{2+}$; $Y=HPO_4{}^{2-}$, $CO_3{}^{2-}$; $X=F^-$, $Cl^-$, $H_2O$; wherein a is an integer of from 0 to 10, b is an integer of from 0 to 6, and c is an integer of from 0 to 2, $Ca(OH)_2$ and CaO. The above-mentioned calcium compounds form stable composites with a protein component, which can easily and stably be crosslinked using crosslinking agents and can excellently be recrystallized with cement. Due to their chemical similarity to endogenous tooth or bone materials, calcium compounds containing phosphate groups are particularly preferred among the above calcium compounds.

Another advantageous embodiment is characterized in that the protein component is selected from the group consisting of collagen, keratin, wheat protein, rice protein, soy protein, almond protein and hydrolysates thereof. The foregoing protein components are highly biocompatible and thus are characterized by high compatibility. Moreover, the precipitation reaction leading to a composite can very easily be induced by a calcium compound, and thus, stable composites are obtained. Among the above-mentioned protein components, gelatine is preferred because gelatine is readily available and yields particularly stable composites. In addition, gelatine be crosslinked very smoothly using a crosslinking agent.

Due to high crosslinking densities, resulting in high hardness values of about 72 HV0.3, and very good processability, the crosslinking agent is preferably selected from the group consisting of the group consisting of transglutaminase, sortase A, tyrosinase, laccase, peroxidase, lysiloxidase, amine oxidase, glutaraldehyde, (1-ethyl-3-(3-dimethylaminopropyl)carbodiimide/N-hydroxysuccinimide, Genipin, caffeic acid, hexamethylene diisocyanate, proanthocyanidin and formaldehyde. Transglutaminase has been found to be particularly advantageous due to excellent crosslinking properties thereof, especially when using gelatine as the protein component.

Particularly suitable degrees of crosslinking of the protein component can be obtained by the advantageous further embodiment wherein the content of crosslinking agent is more than 0 to 25% by mass, especially more than 0 to 10% by mass and especially more than 0 to 4% by mass, in each case based on the total mass of the preparation.

Especially for applications of the preparation in the visual area, it is furthermore advantageous if the preparation is colored and thus will be color-matched to its site of destination. For this purpose, the preparation advantageously contains at least one pigment. The pigment is especially selected from the group consisting of oxides, hydroxides or oxyhydroxides of iron, titanium or zinc and any mixtures thereof, as these inorganic pigments are characterized by very good compatibility and furthermore inertness with respect to the ingredients of the preparation which are essential to the invention. In addition, the preparation may contain X-ray opacifiers to improve X-ray visibility.

For mineralization or remineralization of endogenous dental or bone materials, in particular, the preparation may further advantageously contain at least one water-soluble fluoride, especially $NH_4F$, KF or NaF, the content of water-soluble fluoride being, in particular, more than 0 to 10% by mass and, in particular, more than 0 to 5% by mass, in each case based on the total mass of the preparation.

In the light of further stabilization of the structure of the preparation, the preparation may further advantageously contain casein, the casein content being especially more than 0 to 30% by mass, especially more than 0 to 15% by mass, and especially more than 0 to 5% by mass, in each case based on the total mass of the preparation.

Particularly good biomimetic or bioinspired properties may be achieved if the preparation contains a combination of transglutaminase as a crosslinking agent and casein.

Also described according to the invention is a ready-mix for use in medical or dental applications. Particularly preferred applications in this context are the production of a dental substitute material, a bone substitute material, a root canal sealer, a root filling material, a retrograde filling material, a pulp capping material or a perforation closure material. The ready-mix contains at least one calcium compound selected from the group consisting of calcium phosphates, calcium fluorides and calcium fluorophosphates and hydroxyl derivatives and carbonate derivatives of these calcium salts, calcium hydroxides and calcium oxides, which are combined with at least one protein component, selected from the group consisting of proteins and protein hydrolysates, so as to obtain a composite, at least one solvent, especially including water, and at least one crosslinking agent for the protein component and/or set and/or non-set cement.

According to the present invention, the ready-mix is understood to be a mixture which is directly prepared for processing, i.e. for the corresponding application intended. The ready-mix is required to be processed promptly and, in contrast to the preparation according to the invention, cannot be kept in stock for any length of time. This is especially due to the ingredient "solvent" contained in the ready-mix. Water is preferably used as the solvent. The water can be deionized or distilled or double-distilled water, which is also referred to as MilliQ water, for example.

In all other respects, the ingredients of the ready-mix are comparable to those of the preparation described above and used as intended, with the exception that the ready-mix may contain non-set cement and/or set cement as an alternative or additive to at least one crosslinking agent. Setting of the cement increases stability and strength. Thus, the use of set cement can improve the stability and strength of the ready-mix being formed into a medical or dental product. The set cement is thereby formed upon contact with a suitable solvent, and especially by the solvent added to the ready-mix.

The ready-mix according to the invention can be processed smoothly and with ease and can be reshaped into any medical or dental products or fitted into corresponding body defects or cavities. Due to the ingredients contained in the ready-mix, which are similar in structure and chemical composition to endogenous tooth or bone materials, a highly biocompatible and, moreover, biomimetic or bioinspired product is obtained, which can be combined with endogenous tooth or bone materials in an excellent and permanently stable manner.

The advantages, beneficial effects and further embodiments described for the preparation according to the invention also apply to the ready-mix according to the invention. Consequently, in relation to the advantageous further embodiments of the ready-mix, supplementary reference will also be also made to the advantageous embodiments of the preparation according to the invention.

Thus, calcium silicate cement, calcium phosphate cement as well as mixtures of these cements are also preferred in the ready-mix according to the invention due to the high structural similarities to endogenous tooth or bone materials, with calcium phosphate cement being particularly preferred due to the additional chemical similarity to endogenous tooth or bone materials.

According to another advantageous further embodiment, the calcium compound is selected from the group consisting of $Ca(H_2PO_4)_2 \cdot xH_2O$, wherein x is an integer of from 0 to 6, $CaHPO_4 \cdot xH_2O$, wherein x is an integer of from 0 to 6, $Ca_8(HPO_4)_2(PO_4)_4 \cdot 5H_2O$, $Ca_3(PO_4)_2$, $Ca_{10}(PO_4)_6(OH)_2$, $Ca_{10}(PO_4)_6F_2$, $(Ca_{10-a}M_a)$ $[(PO_4)_{6-b}Y_b]$ $[(OH)_{2-c}X_c]$ wherein M=Na$^+$, Sr$^{2+}$, Mg$^{2+}$, Ba$^{2+}$, Pb$^{2+}$; Y=HPO$_4^{-2}$, CO$_3^{2-}$; X=F$^-$, Cl$^-$, H$_2$O; wherein a is an integer of from 0 to 10, b is an integer of from 0 to 6, and c is an integer of from 0 to 2, $Ca(OH)_2$ and CaO, because these calcium compounds form stable composites that are easily and stably crosslinkable using crosslinking agents and can excellently be recrystallized with cement. Due to their chemical similarity to endogenous dental or bone materials, calcium compounds containing phosphate groups are particularly preferred among the above-mentioned calcium compounds.

Also advantageously, the protein component is selected from the group consisting of collagen, keratin, wheat protein, rice protein, soy protein, almond protein and hydrolysates thereof and is especially gelatine. The foregoing protein components are highly biocompatible, as previously stated, and are thus characterized by a high degree of compatibility. Moreover, precipitation reaction leading to a composite can very smoothly be accomplished by use of a calcium compound, thus obtaining stable composites. Gelatine is particularly preferred among them due to good availability thereof and formation of especially stable composites. In addition, gelatine can very easily be crosslinked further using a crosslinking agent.

Further advantageously, the crosslinking agent is selected from the group consisting of transglutaminase, sortase A, tyrosinase, laccase, peroxidase, lysiloxidase, amine oxidase, glutaraldehyde and (1-ethyl-3-(3-dimethylaminopropyl)carbodiimide/N-hydroxysuccinimide, Genipin, caffeic acid, hexamethylene diisocyanate, proanthocyanidin and formaldehyde, the content of crosslinking agent being especially more than 0 to 25% by mass, especially more than 0 to 10% by mass and especially more than 0 to 4% by mass, in each case based on the total mass of the ready-mix. The abovementioned crosslinking agents allow a high degree of crosslinking to be adjusted particularly easily and processability thereof is excellent.

Furthermore, according to the invention, a medical or dental product (hereinafter referred to as "product") is also described, which is especially suitable for use as a dental substitute material, as a bone substitute material, as a root canal sealer, as a root filling material, as a retrograde filling material, as a pulp capping material or as a perforation sealing material, and is characterized by very good compatibility due to high biomimetic and/or bioinspired properties and thus by permanently good mechanical, chemical and biological properties, especially long-lasting stability and very good bonding properties with endogenous tooth or bone materials. In addition, the product according to the invention is excellently biocompatible.

The product according to the invention contains at least one calcium compound selected from the group consisting of calcium phosphates, calcium fluorides and calcium fluorophosphates and hydroxyl derivatives and carbonate derivatives of these calcium salts, calcium hydroxides and calcium oxides, which is precipitated using at least one protein component selected from the group consisting of proteins and protein hydrolysates, whereby a composite of the calcium compound and the protein component is obtained. In addition, the protein component is crosslinked using at least one crosslinking agent for the protein component and/or the precipitated calcium compound is set with cement. The degree of setting may be adjusted as desired.

The product according to the invention can be obtained by crosslinking and/or setting the ready-mix according to the invention.

Accordingly, reference is made to the ready-mix according to the invention with respect to the advantages, advantageous effects and further embodiments of the product according to the invention.

Advantageously, the cement is selected from the group consisting of calcium silicate cement, calcium phosphate cement and mixtures thereof.

Furthermore, the medical or dental product advantageously uses a calcium compound selected from the group consisting of $Ca(H_2PO_4)_2 \cdot xH_2O$, wherein x is an integer of from 0 to 6, $Ca(H_2PO_4)_2 \cdot xH_2O$, wherein x is an integer of from 0 to 6, $Ca_8(HPO_4)_2(PO_4)_4 \cdot 5H_2O$, $Ca_3(PO_4)_2$, $Ca_{10}(PO_4)_6(OH)_2$, $Ca_{10}(PO_4)_6F_2$, $(Ca_{10-a}M_a)$ $[(PO_4)_{6-b}Y_b]$ $[(OH)_{2-c}X_c]$ wherein M=Na$^+$, Sr$^{2+}$, Mg$^{2+}$, Ba$^{2+}$, Pb$^{2+}$; Y=HPO$_4^{2-}$, CO$_3^{2-}$; X=F$^-$, Cl$^-$, H$_2$O; wherein a is an integer of from 0 to 10, b is an integer of from 0 to 6, and c is an integer of from 0 to 2, $Ca(OH)_2$ and CaO.

Moreover, further advantageously, the protein component is selected from the group consisting of collagen, keratin, wheat protein, rice protein, soy protein, almond protein and hydrolysates thereof and is especially gelatine. In addition, the crosslinking agent is preferably selected from the group consisting of transglutaminase, sortase A, tyrosinase, laccase, peroxidase, lysil oxidase, amine oxidase, glutaraldehyde and (1-ethyl-3-(3-dimethylaminopropyl)carbodiimide/N-hydroxysuccinimide, Genipin, caffeic acid, hexamethylene diisocyanate, proanthocyanidin and formaldehyde, the content of crosslinking agent being in particular more than 0 to 25% by mass, in particular more than 0 to 10% by mass and in particular more than 0 to 4% by mass, in each case based on the total mass of the medical or dental product. Among the above-mentioned crosslinking agents, transglutaminase is particularly preferred.

Further according to the invention, the use of the medical or dental product disclosed above as a filling material for filling dental defects and/or bone defects will be described.

Also according to the invention, a method for producing a medical or dental product will also be described. The medical or dental product may be used as the medical or dental product according to the invention disclosed above, and especially may be used as a tooth substitute material, a bone substitute material, a root canal sealer, a root filling material, a retrograde filling material, a pulp capping material or a perforation closure material.

According to the invention, the method comprises a step of forming a composite compound of at least one calcium compound selected from the group consisting of calcium phosphates, calcium fluorides and calcium fluorophosphates and hydroxyl derivatives and carbonate derivatives of these calcium salts, calcium hydroxides and calcium oxides, and at least one protein component selected from the group consisting of proteins and protein hydrolysates. The composite compound, or in short, the composite, is thus obtained by precipitating the at least one calcium compound with the at least one protein component.

A step of crosslinking the composite compound using at least one crosslinking agent and/or a step of setting the composite compound with non-set cement. The crosslinking agent used is a crosslinking agent for the protein component, which consequently creates crosslinking compounds with the protein component that reinforce the structure of the resulting medical or dental product, thus increasing mechanical, chemical and biological stability thereof. Setting of the composite compound using non-set cement is performed especially by adding a solvent, such as water in particular, which initiates recrystallization of the cement and, depending on the composition, also of the calcium compound, which further improves the structure of the medical or dental product and increases mechanical stability thereof.

The method can be implemented smoothly and without great technical effort, allowing the production of a biomimetic and thus a medical or dental product similar to an endogenous tooth or bone material in terms of chemical composition and structure, having excellent biocompatibility, high mechanical and permanently good stability as well as excellent bondability to endogenous tooth or bone materials.

The advantages, advantageous effects and further embodiments described for the preparation according to the invention, the ready-mix according to the invention and the medical or dental product according to the invention also apply to the method according to the invention for producing a medical or dental product.

Accordingly, the cement is preferably selected from the group consisting of calcium silicate cement, calcium phosphate cement and mixtures thereof and especially is calcium phosphate cement.

A general manufacturing procedure for the production of an apatite-gelatine composite according to the present invention will be given below. For this purpose, the apatite-gelatine composite is prepared by mixing at least one water-soluble calcium salt with at least one water-soluble phosphate in the presence of a protein, wherein a molar ratio of Ca to P is adjusted from 1.5 to 1 to 1.67 to 1, wherein the water-soluble phosphate especially is $NaH_2PO_4 \cdot H_2O$ and wherein the water-soluble calcium salt especially is $CaCl_2$.

EXAMPLES

Unless otherwise stated, percentages given refer to mass %. Furthermore, "$PO_4$" is understood to mean "phosphate" ($PO_43-$).

1. Production of a Composite or Composite Compound 1.1 Production of Calcium Phosphate-Protein Component Composites:

Examples for the preparation of calcium phosphate-protein component composites, i.e. calcium phosphate precipitated using a protein component, are given below. As an example, gelatine is used as the protein component, but other protein components, such as those disclosed above, may also be used.

Example 1

Apatite-Gelatine Composite

More than 0 to 25 g, especially 3 g of gelatine was dissolved in 500 ml of $H_2O$ at 45° C. and then cooled to 25° C. Dissolving gelatine (general: protein component) can generally be done in a temperature range above 0° C. to about 70° C. 45° C. was found to be optimal to quickly obtain a uniformly dissolved gelatine solution. Subsequently, 22.05 g $CaCl_2$-$2H_2O$ (0.15 mol) was added, and generally the amount of $CaCl_2$-$2H_2O$ can be varied throughout the solution range of $CaCl_2$ as long as the molar ratio of Ca to $PO_4$ is adjusted to 1.5 to 1 to 1.67 to 1. Then, the pH of the solution was adjusted to pH 9, although the pH generally can be from 7 to 11 to finally obtain apatite. The solution was stirred for about 30 minutes, causing the solute ions to attach to the gelatine. Thus, a sort of a pre-structurization took place.

In parallel, a second solution was prepared from 12.42 g $NaH_2PO_4$—$H_2O$ (90 mmol) in 250 ml $H_2O$. Again, the molar ratio of Ca to $PO_4$ was variable in the range of from 1.5 to 1 to 1.67 to 1. This second solution was titrated to the first solution at pH kept constant by 1 M NaOH, at about 3 ml/min (0.1 ml to about 20 ml/min is possible). After completion of the addition, stirring was continued at constant pH for another 24 h (another 2 h to 365 days is generally possible), then centrifuged and washed four times with 55° C. $H_2O$. Samples were then either stored under refrigeration for direct use, lyophilized, or dried at 50° C. for hardness measurement.

The particles obtained herein, as long as they were freeze-dried, had a platelet-like structure with a thickness of a few nanometers and an extension of less than 100 nm. A white powder was obtained.

When the platelets were dried at elevated temperature as well as cross-linked, these platelets collapsed and adhered to each other, forming the desired dentin-like structure. In this process, a solid tooth-like material was obtained. Without crosslinking of the protein component, the material obtained had a hardness of approx. 25-30 HV0.3. When crosslinked with transglutaminase and casein, a hardness of up to 72 HV0.3 could be achieved.

The protein content could be varied over a very wide range.

In each case, the hardness measurement was carried out according to Vickers HV0.3: see "Metallic materials—Vickers hardness test—Part 1: Test method (ISO 6507-1: 2018); German version EN ISO 6507-1:2018".

Example 2

Octacalcium Phosphate (OCP)-Gelatine Composite

The synthesis of the OCP-gelatine composites was carried out according to the same principle as the synthesis of the apatite composite. Except the order of calcium and phosphate addition and molar ratio thereof. Thus, in the standard procedure herein, 3 g of gelatine (also variable from more than 0 to about 25 g) was dissolved in 500 ml of $H_2O$ at 45° C. and then cooled to room temperature. Then, 12.42 g of $NaH_2PO_4$—$H_2O$ (90 mmol) was added (the amount of $NaH_2PO_4$—$H_2O$ can be varied throughout the solution range of $NaH_2PO_4$—$H_2O$ as long as the molar ratio of Ca to $PO_4$ is always adjusted to 1.33 to 1), the pH was adjusted to 7 (the pH can be varied in the range of 5 to 7.5 to finally obtain octacalcium phosphate), and stirred for 30 minutes for pre-structurization, resulting in attachment of the dissolved ions to the gelatine.

In parallel, a second solution consisting of 17.64 g $CaCl_2$-$2H_2O$ (0.12 mol) in 250 ml $H_2O$ was prepared (as described above, variable in the ratio to $PO_4$) and, with pH 7 being constant by addition of 1 M NaOH (pH can be varied in the range of pH 5 to 7.5), the calcium chloride solution was added to the phosphate solution at 3 ml/min (variable from 0.1 to 20 ml/min). The solution was then either directly centrifuged as well as washed or stirred for 24 h for maturation (variable from 1 h to 365 days) and then centrifuged/washed as well as freeze-dried as desired. Herein, when freeze-drying, particles having a thickness of a few nm and an extension of several hundred nm were obtained, which were in the form of a white powder.

When drying by elevated temperature, no hard material was obtained herein.

The protein content could be adjusted very well.

Example 3

Brushite-Gelatine Composite 3 g of gelatine (variable from more than 0 to 25 g) was dissolved in 500 ml of $H_2O$ at 45° C. and then cooled to 25° C. (temperatures between 0 and 70° C. are also possible), followed by addition of 17.64 g of $CaCl_2$-$2H_2O$ (0, 12 mol) (the amount of $CaCl_2$-$2H_2O$ can be varied throughout the solution range of $CaCl_2$ as long as the molar ratio of Ca to $PO_4$ is always adjusted to 1 to 1) followed by pH adjustment to pH 5 (can be varied in the range of pH 2 to 5 to finally obtain brushite). The solution was then stirred for half an hour for pre-structurization.

In parallel, a second solution of 16.598 g $NaH_2PO_4$—$H_2O$ (0.12 mol) in 250 ml $H_2O$ was prepared (as described above, variable in relation to Ca), which was titrated at 3 ml/min (variable from 0.1 to 20 ml/min) at pH kept constant by 1 M NaOH after the end of the prestructuring phase. The order of Ca or $PO_4$ addition may also be reversed, i.e. $NaH_2PO_4$—$H_2O$ may also be added and $CaCl_2$ titrated. After completion of the addition, stirring was continued at constant pH for another 24 h (variable between 1 h and 365 days), then centrifuged and washed four times with 55° C. $H_2O$. Samples were then either stored under refrigeration or freeze-dried.

Larger platelets with a thickness of several hundred nm and an extension of 10 to 100 μm were obtained. When freeze-drying as well as drying by elevated temperature, a powder was obtained.

The gelatine content was significantly lower. Only contents up to 5 mass % were obtained.

Example 4

Amorphous Calcium Phosphate (ACP)-Gelatine Composite 3 g of gelatine (variable from more than 0 to 25 g) was dissolved in 500 ml of $H_2O$ at 45° C. and then cooled to 25° C. (other temperatures between 0 and 70° C. are also possible), followed by the addition of 24.51 g of $CaCl_2$-$2H_2O$ (0, 167 mol) (the amount of $CaCl_2$-$2H_2O$ can be varied throughout the solution range of $CaCl_2$) followed by pH adjustment to pH 10 (can be varied in the range of pH 2 to 12 to finally obtain ACP) with subsequent half-hour stirring for pre-structurization.

In parallel, a second solution of 13.799 g $NaH_2PO_4$—$H_2O$ (0.10 mol) in 250 ml $H_2O$ was prepared (the ratio of Ca to $PO_4$ here is variable in molar ratio from 1.2 to 1 to 2.2 to 1), which was titrated at 6 ml/min (variable from 4 to 30 ml/min) at pH kept constant by 1 M NaOH after the end of the prestructuring phase. The order of Ca or $PO_4$ addition may also be reversed, i.e. $NaH_2PO_4$—$H_2O$ may also be added and $CaCl_2$ titrated. After completion of the addition, samples were directly centrifuged and washed four times with 55° C. $H_2O$. Samples were then either lyophilized or dried at 50° C. for hardness measurement.

Partially spherical structures which were very poorly defined were obtained, yielding a white powder upon freeze-drying.

During normal drying, transformation towards apatite occurred, resulting in a solid tooth-like material.

The gelatine content could be adjusted very well. Contents from 0 to 30 mass % were obtained.

2. Production of Medical or Dental Products Using Biomimetic Dental Cements/Biomimetic Filling Materials as an Example General Production Process when Employing Calcium Phosphate Cements:

For the production of biomimetic dental cements according to the invention, different calcium compounds selected from calcium phosphate phases were used in combination with the previously described calcium phosphate-gelatine composites to achieve recrystallization towards an apatite phase having a biomimetic structure by combining calcium-rich phases and calcium-poor phases.

Parallel to curing of the cement materials initiated by the inorganic phase, an additional curing step was carried out herein by crosslinking the gelatine (protein component) contained with various crosslinkers, in particular with transglutaminase in combination with casein. This second additional crosslinking step, in addition to the setting reaction by recrystallization, significantly contributed to the good mechanical, chemical and biological properties as well as the excellent long-term stability of the dental filling material.

FIG. 2 reviews the achieved hardnesses of composites crosslinked with different crosslinking agents.

In a typical experiment, various calcium salts having different calcium contents as well as phosphate-containing salts (all salts listed in Table 1 can be used in all possible compositions) were mixed such that a molar ratio of calcium to phosphate of 1.5 to 1 to 1.67 to 1 was adjusted, with the ratio of 1.67 to 1 being preferred, since this corresponds to the ratio in pure apatite.

The salts were used in this process by grinding them into various particle sizes between 100 μm and 1 nm in order to change the reaction rates and properties of the materials. In addition to the calcium phosphate salts, a proportion of previously synthesized calcium phosphate composite was added and then crosslinked with a crosslinker during curing to form an organic supporting network. In addition, it was always possible to add further additives to improve the structure, for example by defoaming or adding fluoride, or to increase the radiopacity, for example by adding radiopaque materials, and to adapt the product to the tooth color using a dye.

TABLE 1

Overview of compounds for producing calcium phosphate-gelatine composites and dental cements from calcium phosphate cements and composite.

| Possible reactants | Molecular formula | Ca/$PO_4$ ratio |
|---|---|---|
| Phosphoric acid | $H3PO_4$ | 0 (100% $PO_4$) |
| Salt of the phosphoric acid | $AxByPO_4$ | 0 (100% $PO_4$) |
| Monocalciumphosphate monohydrate (MCPM) | $Ca(H2PO_4)•H_2O$ | 0.5 |

TABLE 1-continued

Overview of compounds for producing calcium phosphate-gelatine composites
and dental cements from calcium phosphate cements and composite.

| Possible reactants | Molecular formula | Ca/PO$_4$ ratio |
|---|---|---|
| Monocalciumphosphate x hydrate | Ca(H2PO$_4$)•$x$H$_2$O | 0.5 |
| Monocalciumphosphate anhydrous (MCPA) | Ca(H2PO$_4$) | 0.5 |
| Brushite (dicalciumphosphate dihydrate) | CaHPO$_4$•H$_2$O | 1 |
| Brushite-gelatine composite | CaHPO$_4$•H$_2$O + gelatine | 1 |
| Monetite (dicalciumphosphate anhydrous) | CaHPO$_4$ | 1 |
| Octacalciumphosphate (OCP) | Ca8(HPO$_4$)2(PO$_4$)4•5H$_2$O | 1.33 |
| Octacalciumphosphate-Gelatine-Composite | Ca8(HPO$_4$)2(PO$_4$)4•5H$_2$O + Gelatine | 1.33 |
| α-/β- Tricalciumphosphate (TCP) | Ca$_3$(PO$_4$)$_2$ | 1.5 |
| Hydroxyapatite (HAP) | Ca$_{10}$(PO$_4$)$_6$(OH)$_2$ | 1.667 |
| Apatite | (Ca, Ba, Pb, Sr, etc.)5(PO$_4$, HPO$_4$, CO3)3(F, Cl, OH) | 1.33-1.667 (or more than 1.67) |
| Fluorapatite (FAP) | Ca$_{10}$(PO$_4$)$_6$F$_2$ | 1.667 |
| HAP/FAP-Gelatine-Composite | Ca$_{10}$(PO$_4$)$_6$(OH)$_2$ + gelatine | 1.667 |
| Tetracalciumphosphate (TTCP) | Ca4(PO$_4$)2O | 2 |
| Amorphous calciumphosphates (ACP) | Ca$x$H$y$(PO$_4$)$z$•$n$H$_2$O, n = 3-4.5; | 1.2-2.2 |
| ACP-Gelatine Composite | | 1.2-2.2 |
| Calciumhydroxide | Ca(OH)2 | 100% Ca |
| Calciumoxide | CaO | 100% Ca |
| Calcium salts | Ca(A$x$B$y$) | 100% Ca |

Example 5

Production of Biomimetic Dental Cements Based on Wet Apatite-Gelatine Composites For producing a biomimetic dental cement using wet apatite-gelatine composites, the procedure was to dry mix calcium-containing as well as phosphate-containing salts in a Ca/PO$_4$ molar ratio of 1.667 to 1 or to grind them together. In addition to the calcium or phosphate salts, a proportion of fluoride-containing salts or carbonate-containing salts could be added to obtain fluorapatite-substituted or carbonate-substituted apatite. After mixing all the dry materials, an amount of wet apatite-gelatine composite (in different compositions in terms of protein and water content) and, if necessary, water were then added to obtain a processable paste. Addition of water initiated the reaction between the salts used towards the apatite and curing of the entire material.

In parallel with the addition of the composite material, the use of gelatine-crosslinking agents (see FIG. 2) in varying proportions was able to achieve additional curing of the composite material, thus further improving the material properties.

A specific example thereof given the following is the formation of the biomimetic dental cement based on wet apatite-gelatine composites:

0.7 g α-tricalcium phosphate (2.26 mmol) having an average particle size in the range of 1-10 μm was dry-triturated together with 0.042 g CaO (0.75 mmol) as well as 0.0252 g NaF (0.6 mmol). In parallel, a second mixture consisting of 0.233 g wet apatite-gelatine composite (water content 75%; protein content 5%; apatite content 20%) together with 0.017 g transglutaminase (for example "ultrafiltration" from Ajinomoto Activa WM) as well as 0.0085 g casein and 0.15 ml H$_2$O was mixed for 20 seconds in the universal mixer. Both phases were then mixed together in the universal mixer for 30 seconds, resulting in a biomimetic restorative material having an initial pH of 12 that was easy to apply and cured (according to ISO 6876:2012) within 5 to 60 minutes, depending on the particle size. During this process, compressive strengths of up to 51 MPa could be achieved when determined according to ISO 9917-1:2007 (E). Furthermore, solubilities of less than 3% and flowabilities of 16 mm to 21 mm (depending on water addition) (ISO 6876:2012) could be achieved.

Example 6

Preparation of Biomimetic Dental Cements Based on Freeze-Dried Apatite-Gelatine Composites The procedure here was basically the same as for the wet apatite-gelatine composites, except that here the mixing and grinding of all dry components could take place before the addition of water, since the dried composite did not yet initiate cementation of the calcium salts and phosphate salts. The reaction was then only initiated by the addition of water, resulting in good shelf life of the cement mixture.

A specific example thereof given in the following is the formation of the biomimetic dental cement based on freeze-dried apatite-gelatine composites:

0.7 g α-tricalcium phosphate (2.26 mmol) having an average particle size in the range of 1-10 μm was dry-triturated together with 0.042 g CaO (0.75 mmol) as well as 0.0252 g NaF (0.6 mmol). In parallel, a second mixture consisting of 0.04 g of freeze-dried apatite-gelatine composite (protein content 20%; apatite content 80%) together with 0.017 g of transglutaminase (e.g. "ultrafiltration" from Ajinomoto Activa WM) as well as 0.0085 g of casein and 0.3 ml of $H_2O$ were mixed together for 20 seconds in the universal mixer. Both phases were then mixed in the universal mixer for 30 seconds, resulting in an easy-to-apply and fast-curing biomimetic filling material.

Example 7

Preparation of Biomimetic Dental Cements Based on Wet Octacalcium Phosphate-Gelatine Composites For the preparation of a biomimetic dental cement based on wet octacalcium phosphate-gelatine composites, the inorganic content, as well as gelatine and water content of the composites were first determined. On the basis of the calcium and phosphate contents thus obtained (for OCP: $Ca/PO_4=1.33$ to 1) in relation to gelatine and water, it was then possible to adjust the use of calcium-containing and phosphate-containing salts such that a molar calcium to phosphate ratio of 1.5 to 1 to 1 was obtained within the entire cement composition, with 1.67 to 1 being preferred in a standard experiment (in this case, the ratio of calcium compound to protein component could be varied over the entire range). Procedurally, this was performed by grinding all dry calcium salts as well as phosphate salts and possible added fluorine- or carbonate-containing salts, either before blending thereof or afterwards. The mixing of the dry ingredients was then followed by the addition of the wet composites and, if necessary to achieve the desired viscosity, water and a gelatine crosslinker. The entire mass was then thoroughly mixed once again and could then be applied as a restorative material.

A specific example thereof is the formation of the biomimetic dental cement based on wet octacalcium phosphate-gelatine composites in the following:

0.7 g $\alpha$-tricalcium phosphate (2.26 mmol) having an average particle size in the range of 1-10 $\mu$m was dry-triturated together with 0.044 g CaO (0.97 mmol) as well as 0.0252 g NaF (0.6 mmol). In parallel, a second mixture consisting of 0.25 g wet OCP gelatine composite (water content 75%; protein content 5%; octacalcium phosphate content 20%) together with 0.017 g transglutaminase (ultra-filtration from Ajinomoto Activa WM) as well as 0.0085 g casein and 0.15 ml $H_2O$ was mixed for 20 seconds in a universal mixer. Both phases were then mixed together in the universal mixer for 30 seconds, resulting in an easy-to-apply and fast-curing biomimetic filling material having an initial pH of 12.

Example 8

Production of Biomimetic Dental Cements Based on Freeze-Dried Octacalcium Phosphate-Gelatine Composites Basically, the procedure for the production of biomimetic dental cements based on freeze-dried OCP-gelatine composites was similar to that of the wet OCP-gelatine composites. Again, the proportion of OCP to the total mass of the composite was determined to determine the addition of calcium and phosphate containing salts, with which the Ca to $PO_4$ molar ratio of 1.5 to 1.67 to 1 was obtained at the end. The difference with the wet composites was that water was added to start the reaction.

A specific example thereof given in the following is the formation of the biomimetic dental cement based on freeze-dried octacalcium phosphate gelatine composites:

0.7 g $\alpha$-tricalcium phosphate (2.26 mmol) having an average particle size in the range of 1-10 $\mu$m was dry-triturated together with 0.044 g CaO (0.97 mmol) as well as 0.0252 g NaF (0.6 mmol). In parallel, a second mixture consisting of 0.06 g of freeze-dried OCP-gelatine composite (protein content 20%; octacalcium phosphate content 80%) together with 0.017 g of transglutaminase (ultrafiltration from Ajinomoto Activa WM) as well as 0.0085 g of casein and 0.3 ml of $H_2O$ was mixed for 20 seconds in a universal mixer. Both phases were then mixed together in the universal mixer for 30 seconds, resulting in an easy-to-apply and fast-curing biomimetic filling material having an initial pH of 12.

Example 9

Production of Biomimetic Dental Cements Based on Wet Brushite-Gelatine Composites For the production of a dental cement based on wet brushite-gelatine composites, the content of calcium, phosphate, gelatine, as well as water was determined, as in the case of the previously described OCP-based cements to calculate addition of the other calcium as well as phosphate-containing salts based on this result, to finally obtain the molar ratio of calcium to phosphate of 1.5-1.667 to 1 as well as a suitable viscosity in the final cement material. Brushite had a molar ratio of $Ca/PO_4$ of 1 to 1. The ratio adjusted to apatite by the other salts was such that, in addition to the conversion of the salts to apatite, the composite was also converted to apatite, thus achieving direct bonding of the inorganic components throughout the entire system. In parallel, the material properties could also be further improved herein by the addition of fluorine- or carbonate-containing salts. In order to also obtain a network of the organic component of the gelatine, or more generally of the protein components, the use of crosslinkers of the protein component, which was carried out in parallel during the addition of the aqueous component, was also advantageous for the formation of the most durable dental cement material possible.

A specific example thereof given in the following is the formation of the biomimetic dental cement based on wet brushite-gelatine composites:

0.7 g of $\alpha$-tricalcium phosphate (2.26 mmol) having an average particle size ranging from 1 to 10 $\mu$m was dry-triturated together with 0.052 g of CaO (0.97 mmol) as well as 0.0252 g of NaF (0.6 mmol). In parallel, a second mixture consisting of 0.25 g wet brushite-gelatine composite (water content 80%; protein content 1%; octacalcium phosphate content 19%) together with 0.017 g transglutaminase (ultra-filtration from Ajinomoto Activa WM) as well as 0.0085 g casein and 0.15 ml $H_2O$ was mixed for 20 seconds in a universal mixer. Both phases were then mixed together in the universal mixer for 30 seconds, resulting in an easy-to-apply and fast-curing biomimetic filling material having an initial pH of 12.

Example 10

Preparation of Biomimetic Dental Cements Based on Freeze-Dried Brushite-Gelatine Composites For dental cements based on freeze-dried brushite-gelatine composites, the same method was used as for the wet version. After determining the gelatine content of the dry composites, a suitable mixture of calcium and phosphate salts was selected and mixed together in the dry state to convert the brushite portion to apatite. Again, the addition of fluoride or carbonate containing salts could lead to another improvement of the cement properties, followed by the addition of water to achieve a suitable viscosity. To improve the properties of the cements, it was also advantageous herein to add a crosslinker to the dry material before adding the water.

A specific example thereof given in the following is the formation of the biomimetic dental cement based on freeze-dried brushite-gelatine composites:

0.7 g α-tricalcium phosphate (2.26 mmol) having an average particle size in the range of 1-10 μm was dry-triturated together with 0.052 g CaO (0.97 mmol) as well as 0.0252 g NaF (0.6 mmol). In parallel, a second mixture consisting of 0.05 g of lyophilized brushite-gelatine composite (protein content 5%; brushite content 95%) together with 0.017 g of transglutaminase (ultrafiltration from Ajinomoto Activa WM) as well as 0.0085 g of casein and 0.3 ml of $H_2O$ was mixed for 20 seconds in the universal mixer. Both phases were then mixed together in the universal mixer for 30 seconds, resulting in an easy-to-apply and fast-curing biomimetic filling material having an initial pH of 12.

Example 11

Preparation of Biomimetic Dental Cements Based on Wet Amorphous Calcium Phosphate-Gelatine Composites As amorphous calcium phosphates are able cover a very wide range of calcium to phosphate ratios from 1.2 to 1 up to 2.2 to 1, the composition, with regard to calcium, phosphate, protein component and water, was precisely determined for each newly synthesized composite to adjust the other calcium and phosphate-containing salts used on the basis of these results used to adjust a calcium to phosphate ratio of 1.5-1.667 to 1. Due to the water content of the composites as well as additionally added water, a suitable viscosity could be adjusted. By adding the other calcium- and phosphate-containing salts and adjusting them to the ratio suitable for apatite, it was possible to initiate crystallization of the amorphous composite phase to apatite, thus achieving hardening of the cement. Addition of fluoride-containing salts could also accelerate the transformation to fluorapatite.

The Formation of the Biomimetic Dental Cement Based on Wet Amorphous Calcium Phosphate-Gelatine Composites:

0.7 g α-tricalcium phosphate (2.26 mmol) having an average particle size in the range of 1-10 μm was dry-triturated together with 0.042 g CaO (0.75 mmol) as well as 0.0252 g NaF (0.6 mmol). In parallel, a second mixture consisting of 0.233 g wet amorphous calcium phosphate-gelatine composite (water content 80%; protein content 4%; calcium phosphate content 16%, Ca/$PO_4$ ratio 1.67 to 1) together with 0.017 g transglutaminase (e.g. "ultrafiltration" from Ajinomoto Activa WM) as well as 0.0085 g casein and 0.15 ml $H_2O$ were mixed for 20 seconds in the universal mixer. Both phases were then mixed in the universal mixer for 30 seconds, resulting in an easy-to-apply and fast-curing biomimetic filling material.

Example 12

Production of Biomimetic Dental Cements Based on Freeze-Dried Amorphous Calcium Phosphate-Gelatine Composites For dental cements based on freeze-dried amorphous calcium phosphate-gelatine composites, the same method was used as for the wet version. After determining the gelatine content of the dry composites, a suitable mixture of calcium and phosphate salts was selected and mixed together in the dry state. An addition of fluoride-containing or carbonate-containing salts could also be added to this mixture, followed by the addition of water to adjust a suitable viscosity. To improve the properties of the cements, it was also advantageous here to add a gelatine crosslinker to the dry material before adding the water.

A specific example thereof given in the following is the formation of the biomimetic dental cement based on freeze-dried amorphous calcium phosphate-gelatine composites:

0.7 g α-tricalcium phosphate (2.26 mmol) having an average particle size in the range of 1-10 μm was dry-triturated together with 0.042 g CaO (0.75 mmol) as well as 0.0252 g NaF (0.6 mmol). In parallel, a second mixture consisting of 0.04 g of freeze-dried amorphous calcium phosphate-gelatine composite (protein content 20%; calcium phosphate content 80%; Ca/$PO_4$ ratio 1.67 to 1) together with 0.017 g of transglutaminase (e.g. "ultrafiltration" from Ajinomoto Activa WM) as well as 0.0085 g of casein and 0.3 ml of $H_2O$ was mixed for 20 seconds in the universal mixer. Both phases were then mixed in the universal mixer for 30 seconds, resulting in an easy-to-apply and fast-curing biomimetic filling material.

Example 13

Production of Cements Based on Calcium Phosphate-Gelatine Composites and Calcium Silicates The calcium phosphate-gelatine composites obtained were mixed with cements containing calcium silicate to cure them under conditions similar to those found in the human oral cavity. The advantage of this approach was that the wet, swollen composites were thus cured by the water consumption of the setting reaction of the cement, while the cement provided an additional curing and stabilizing component. Again, additional crosslinkers of the gelatine contained were of particular advantage for the material properties of the filling materials.

Example 14

Reaction of Wet Apatite-Gelatine Composites with Calcium Silicates

Apatite-gelatine composites were cured by the use of calcium silicates to the extent that all water bound in the composites was consumed by the cement added in the setting reaction thereof, thereby curing the cement.

For this purpose, wet apatite-gelatine composites (in different compositions in terms of protein and water content) were used. According to the water contained, Portland cement was added in ratios between 1 mass % and 99 mass %, so that an easily moldable and applicable mass was obtained. In addition to setting by hardening of the inorganic components, another gelatine crosslinker could be added to the cement mass, which further beneficially affected the mechanical properties.

A specific example thereof given in following is the formation of the bioinspired dental cement based on wet apatite-gelatine composites in combination with calcium silicate:

0.0833 g $Ca_2SiO_4$ (0.51 mmol) having an average particle size in the range of 1-10 μm was dry-triturated together with 0.1667 g $Ca_3SiO_5$ (0.73 mmol) having an average particle size of 1-10 μm as well as 0.01 g NaF. In parallel, a second mixture consisting of 0.125 g wet apatite-gelatine composite (water content 75%; protein content 5%; apatite content 20%) together with 0.009 g transglutaminase (e.g. "ultrafiltration" from Ajinomoto Activa WM) and 0.0045 g casein and 0.12 ml $H_2O$ was mixed for 20 seconds in the universal mixer. Both phases were then mixed for 30 seconds in the universal mixer, resulting in an easy-to-apply and fast-curing biomimetic filling material with curing times between 30 minutes and 5 h, depending on the particle size. During this process, compressive strengths of up to 52 MPa could be achieved when determined according to ISO 9917-1:2007 (E). Furthermore, solubilities of below 7% and flowabilities of 15 mm-27 mm (depending on water addition) (ISO 6876:2012) could be achieved.

Example 15

Reaction of Freeze-Dried Apatite-Gelatine Composites with Calcium Silicates

Freeze-dried apatite-gelatine composites were mixed with Portland cement at mixing ratios of 1%-99% (W/W) and blended with water in proportions of 10-70 mass % to obtain a paste-like mass. Curing the cementitious materials obtained herein was caused by the simultaneous swelling of the apatite-gelatine composites and recrystallization or setting of the Portland cement. During this process, addition of a gelatine crosslinker was also beneficial herein to the mechanical properties (hardness) of the dental cement.

A specific example thereof given in the following is the formation of the bioinspired dental cement based on freeze-dried apatite-gelatine composites in combination with calcium silicate:

0.0833 g $Ca_2SiO_4$ (0.51 mmol) having an average particle size in the range of 1-10 μm was dry-triturated together with 0.1667 g $Ca_3SiO_5$ (0.73 mmol) having an average particle size of 1-10 μm and 0.01 g NaF. In parallel, 0.04 g of freeze-dried apatite-gelatine composite (protein content 20%; apatite content 80%) was mixed together with 0.017 g of transglutaminase (e.g. "ultrafiltration" from Ajinomoto Activa WM) as well as 0.0085 g of casein and 0.3 ml of $H_2O$ for 20 seconds in a universal mixer. Both phases were then mixed in the universal mixer for 30 seconds, resulting in an easy-to-apply and fast-curing bioinspired filling material.

Example 15

Reaction of Wet Octacalcium Phosphate-Gelatine Composites with Calcium Silicates Portland cement curing of the octacalcium phosphate-gelatine composites used was based on two parallel mechanisms. In a first step, the Portland cement removed the water from the OCP-gelatine composite during setting reaction thereof, resulting in the curing of the total mass. As a second curing step, the recrystallization of the octacalcium phosphate to apatite could be achieved, since calcium hydroxide was formed during the setting reaction of the Portland cement, which provided calcium ions in high excess for the recrystallization of the OCP in an aqueous environment. Thus, the simultaneous reactions provided a high degree of bonding between the two different reactants.

In this reaction, octacalcium phosphate-gelatine composites with gelatine concentrations between 1% and 50% and water contents between 1% and 99% were used and mixed with proportions of Portland cement between 1% and 99% for curing.

Parallel to the inorganic setting, it was also possible herein to achieve curing of the organic component by crosslinking the gelatine.

A specific example thereof given in the following is the formation of the bioinspired dental cement based on wet apatite-gelatine composites in combination with calcium silicate:

0.0833 g $Ca_2SiO_4$ (0.51 mmol) having an average particle size in the range of 1-10 μm was dry-triturated together with 0.1667 g $Ca_3SiO_5$ (0.73 mmol) having an average particle size of 1-10 μm as well as 0.01 g NaF. In parallel, 0.125 g wet octacalcium phosphate-gelatine composites (water content 75%; protein content 5%; OCP content 20%) were mixed together with 0.017 g transglutaminase (ultrafiltration from Ajinomoto Activa WM) as well as 0.0085 g casein and 0.12 ml $H_2O$ for 20 seconds in a universal mixer. Both phases were then mixed in the universal mixer for 30 seconds, resulting in an easy-to-apply and fast-curing bioinspired filling material.

Example 17

Freeze-Dried Octacalcium Phosphate Gelatine Composites

Freeze-dried octacalcium phosphate gelatine composites with gelatine concentrations in the range of 1-50 wt % were blended with Portland cement at mixing ratios of 1-99 wt % (W/W) and mixed with water to obtain a paste-like mass. Curing of the cementitious materials obtained here proceeded by the simultaneous swelling of the gelatine components and recrystallization of the OCP gelatine composites to apatite and the parallel setting of the Portland cement. During this process, addition of a gelatine crosslinker was also beneficial to the mechanical properties of the dental cement, as a stable supporting organic network was obtained.

A specific example thereof given in the following is the formation of the bioinspired dental cement based on freeze-dried OCP gelatine composites in combination with calcium silicate:

0.0833 g $Ca_2SiO_5$ (0.51 mmol) having an average particle size in the range of 1-10 μm was dry-triturated together with 0.1667 g $Ca_3SiO_5$ (0.73 mmol) having an average particle size of 1-10 μm and 0.01 g NaF. In parallel, 0.04 g of freeze-dried OCP-gelatine composite (protein content 20%; OCP content 80%) was mixed together with 0.017 g of transglutaminase (ultrafiltration from Ajinomoto Activa WM) as well as 0.0085 g of casein and 0.3 ml of $H_2O$ for 20 seconds in a universal mixer. Both phases were then mixed in the universal mixer for 30 seconds, resulting in an easy-to-apply and fast-curing bioinspired filling material.

Example 18

Wet Brushite Gelatine Composites

Portland cement curing of the Brushite gelatine composites used was based on two parallel mechanisms. First, the Portland cement removed the water from the brushite-gelatine composite during setting reaction thereof, resulting in curing of the composite portion by drying in parallel with curing of the cement. As a second parallel curing step, recrystallization of the brushite to apatite could be achieved herein, as calcium hydroxide was formed during the setting reaction of the Portland cement, which in an aqueous environment provided calcium ions in high excess for the recrystallization of the brushite. The simultaneous reactions resulted in a high degree of bonding between the two different reactants.

In this reaction, brushite-gelatine composites with gelatine concentrations between 1 mass % and 50 mass % and water content between 1 mass % and 90 mass % were used and mixed with proportions of Portland cement between 1 mass % and 99 mass % for curing.

Parallel to the inorganic setting, it was also possible here to achieve curing of the organic component by crosslinking the gelatine.

A specific example thereof given in the following is the formation of the bioinspired dental cement based on wet brushite-gelatine composites in combination with calcium:

0.0833 g $Ca_2SiO_4$ (0.51 mmol) having an average particle size in the range of 1-10 μm was dry-triturated together with 0.1667 g $Ca_3SiO_5$ (0.73 mmol) having an average particle size of 1-10 μm as well as 0.01 g NaF. In parallel, 0.125 g wet Brushite gelatine composites (water content 70%; protein content 1%; OCP content 29%) were mixed together with 0.017 g transglutaminase (ultrafiltration from Ajinomoto Activa WM) as well as 0.0085 g casein and 0.15 ml $H_2O$ for 20 seconds in a universal mixer. Both phases were subsequently mixed in the universal mixer for 30 seconds, resulting in an easy-to-apply and fast-curing bioinspired filling material.

Example 19

Freeze-Dried Brushite-Gelatine Composites

Freeze-dried brushite-gelatine composites were blended with Portland cement at mixing ratios ranging from 1 mass % to 99 mass % (W/W) and mixed with water to obtain a paste-like mass. Curing of the cementitious materials obtained herein proceeded by the simultaneous swelling and recrystallization of the brushite-gelatine composites and the parallel recrystallization and setting of the Portland cement. During this process, the addition of a gelatine crosslinker was also beneficial for the properties of the dental cement.

A specific example thereof given in the following is the formation of the bioinspired dental cement based on freeze-dried brushite-gelatine composites in combination with calcium silicate:

0.0833 g $Ca_2SiO_4$ (0.51 mmol) having an average particle size in the range of 1-10 μm was dry-triturated together with 0.1667 g $Ca_3SiO_5$ (0.73 mmol) having an average particle size of 1-10 μm and 0.01 g NaF. In parallel, 0.04 g of freeze-dried brushite-gelatine composite (protein content 5%; brushite content 95%) was mixed together with 0.017 g of transglutaminase (ultrafiltration from Ajinomoto Activa WM) as well as 0.0085 g of casein and 0.3 ml of $H_2O$ for 20 seconds in a universal mixer. Both phases were then mixed in the universal mixer for 30 seconds, resulting in an easy-to-apply and fast-curing bioinspired filling material.

Further details, advantages and features of the present invention will be apparent from the following description of embodiments based on the drawing, wherein:

FIG. 1 shows a schematic diagram of the steps in a process for producing a medical or dental product according to one embodiment. Medical or dental products especially are dental substitute materials, bone substitute materials, root canal sealers, root filling materials, retrograde filling materials, pulp capping materials or perforation sealing materials.

The process comprises a first step 100 of forming a composite compound of at least one calcium compound selected from the group consisting of: Calcium phosphates, calcium fluorides and calcium fluorophosphates and hydroxyl derivatives and carbonate derivatives of these calcium salts, calcium hydroxides and calcium oxides and at least one protein component selected from proteins and protein hydrolysates. Herein, the calcium compound is precipitated in the presence of the protein component.

This may be followed by process step 200, wherein crosslinking of the composite compound using at least one crosslinking agent is carried out. The crosslinking agent is preferably selected from the group consisting of: transglutaminase, sortase A, tyrosinase, laccase, peroxidase, lysiloxidase, aminoxidase, glutaraldehyde and (1-ethyl-3-(3-dimethylaminopropyl)carbodiimide/N-hydroxysuccinimide, genipin, caffeic acid, hexamethylene diisocyanate, proanthocyanidin and formaldehyde, wherein casein may be added additively during crosslinking.

The material is then cured to obtain the medical product by added or contained water.

Alternatively or in addition to the process step 200, setting the composite compound with uncured cement to further improve the hardness of the product to be produced, may occur as a process step 300. Preferably, the cement is selected from the group consisting of calcium silicate cement, calcium phosphate cement and mixtures thereof.

Figure 2:
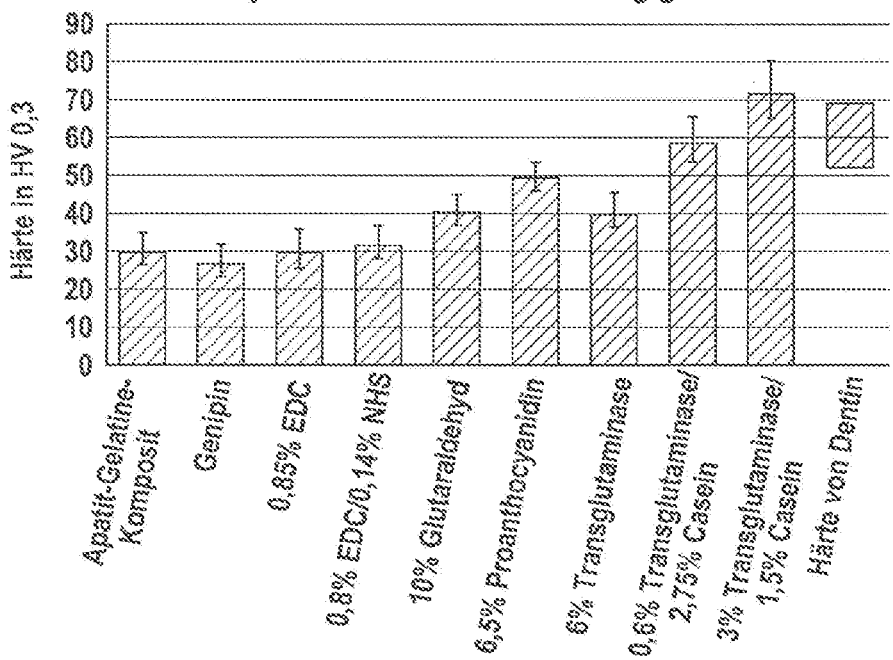
FIG. 2 is an overview of curing achieved with different crosslinkers.

FIG. 2 shows an overview of hardnesses achieved with different crosslinkers, which were determined according to Vickers HV0.3 with a Zeiss Miniload and Hardsoft measuring system. The hardness measurement was thus performed according to Vickers HV0.3 in each case, see "Metallic materials—Hardness testing according to Vickers—Part 1: Test method (ISO 6507-1:2018); German version EN ISO 6507-1:2018".

The figure shows the effect of an aqueous solution of a crosslinker on the hardness of the composite material. Herein, the procedure was that two grams of a wet apatite composite (water content 75%; protein content 5%; apatite content 20%) were crosslinked with 10 ml of a crosslinker solution indicated in the diagram for 24 h. The samples were then centrifuged and dried in an oven at 50° C., cut and polished, and their hardness subsequently was determined at room temperature. The results clearly show that a mixture of transglutaminase (e.g. from Ajinomoto Activa WM after ultrafiltration through a 10000M sieve) and casein provides the best crosslinking properties and thus high hardness. In this context, the mixture of 3% transglutaminase and 1.5% casein should be particularly highlighted, since this, in combination with the apatite composite, results in a hardness of the material which is above the hardness of dentin.

Figure 3:
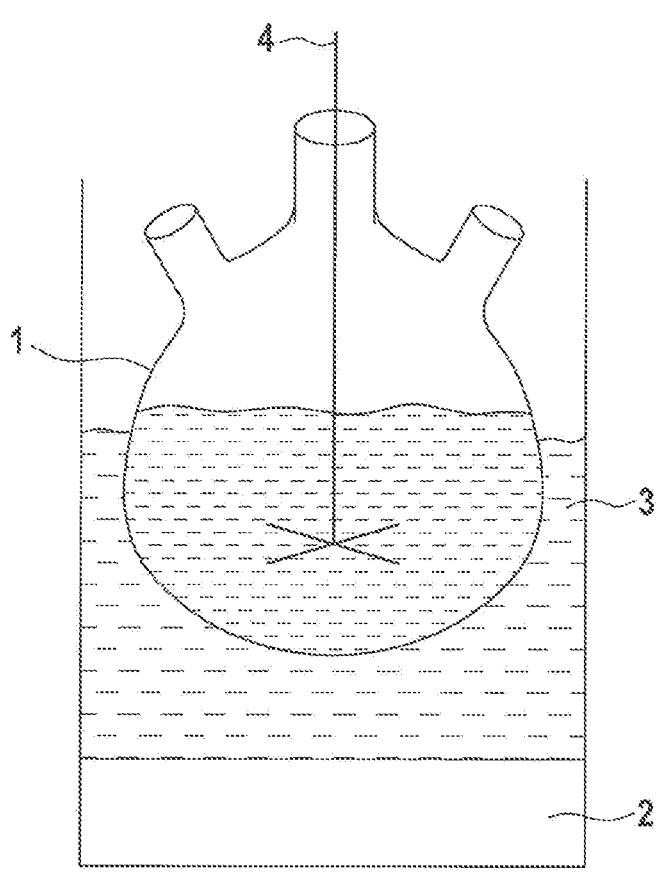
FIG. 3 is a schematic representation of a test set-up for the production of calcium phosphate-protein component composites.

FIG. 3 is a schematic representation of an experimental set-up for the preparation of calcium phosphate-protein component composites. At least one protein component dissolved in water and a calcium compound are placed in a water bath 3 which is temperature-controlled by a heating device 2. Alternatively, a protein component and a phosphate compound may also be introduced. With the provision that a calcium compound has been introduced, at least one phosphate-containing compound is subsequently added. Provided that a phosphate-containing compound has been submitted, at least one calcium compound is subsequently added. In addition, the pH of the solution can be brought into a desired range and maintained by adding an acid or an alkali. A stirrer 4 is provided in the vessel 1 for stirring at the desired speed.

Figure 1:
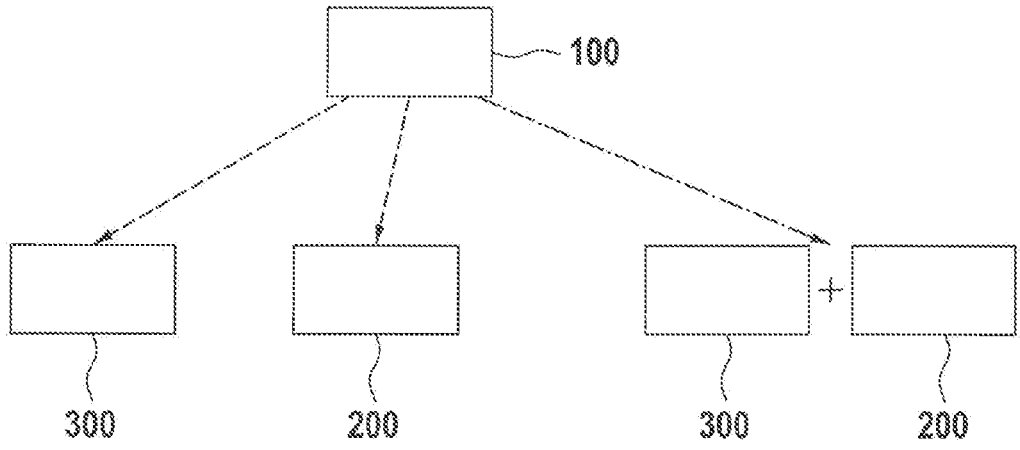
FIG. 1 is a process schematic schematizing the process steps for the production of a medical or dental product according to one embodiment.

In addition to the foregoing written description of the invention, explicit reference is hereby made to the graphic representation of the invention in FIGS. 1 to 3 for supplementary disclosure thereof.

LIST OF REFERENCE NUMBERS

1 Vessel
2 Heating device
3 Water bath
4 Stirrer
100-300 Process steps
The invention claimed is:

1. A preparation comprising:
at least one calcium compound selected from the group consisting of: calcium phosphates, calcium fluorides and calcium fluorophosphates and hydroxyl derivatives and carbonate derivatives of these calcium salts, calcium hydroxides and calcium oxides, which is precipitated using at least one protein component selected from proteins and protein hydrolysates,
at least one cross-linking agent for the at least one protein component, wherein the at least one cross-linking agent is selected from the group consisting of: transglutaminase, sortase A, tyrosinase, laccase, peroxidase, lysiloxidase, amine oxidase, glutaraldehyde, (1-ethyl-3-(3-dimethylaminopropyl)carbodiimide/N-hydroxysuccinimide, Genipin, caffeic acid, hexamethylene diisocyanate, proanthocyanidin and formaldehyde, and
an unset cement.

2. The preparation according to claim 1, wherein the unset cement is selected from the group consisting of calcium silicate cement, calcium phosphate cement, and mixtures of calcium silicate cement and calcium phosphate cement.

3. The preparation according to claim 1, wherein the at least one calcium compound is selected from the group consisting of:
$Ca(H_2PO_4)_2 \cdot xH_2O$, wherein x is an integer of from 0 to 6,
$CaHPO_4 \cdot xH_2O$, wherein x is an integer of from 0 to 6,
$Ca_8(HPO_4)_2(PO_4)_4 \cdot 5H_2O$, $Ca_3(PO_4)_2$, $Ca_{10}(PO_4)_6$ $(OH)_2$, $Ca_{10}(PO_4)_6F_2$, $(Ca_{10-a}M_a)$ $[(PO_4)_{6-b}Y_b]$ $[(OH)_{2-c}X_c]$ wherein $M=Na^+$, $Sr^{2+}$, $Mg^{2+}$, $Ba^{2+}$, $Pb^{2+}$; $Y=HPO_4^{2-}$, $CO_3^{2-}$; $X=F^-$, $Cl^-$, $H_2O$; wherein a is an integer of from 0 to 10, b is an integer of from 0 to 6, and c is an integer of from 0 to 2, $Ca(OH)_2$ and CaO.

4. The preparation according to any one of claim 1, wherein the at least one protein component is selected from the group consisting of: collagen, keratin, wheat protein, rice protein, soy protein, almond protein and hydrolysates thereof.

5. The preparation according to claim 1, wherein the at least one protein component is gelatin.

6. The preparation according to claim 1, wherein a content of the at least one cross-linking agent in the preparation is more than 0 to 25% by mass, based on a total mass of the preparation.

7. The preparation according to claim 1, wherein a content of the at least one cross-linking agent in the preparation is more than 0 to 10% by mass based on a total mass of the preparation.

8. The preparation according to claim 1, wherein a content of the at least one cross-linking agent in the preparation is more than 0 to 4% by mass, based on a total mass of the preparation.

9. The preparation according to claim 1, and further comprising at least one pigment selected from the group consisting of oxides, hydroxides or oxyhydroxides of iron, titanium or zinc and any mixtures of oxides, hydroxides or oxyhydroxides of iron, titanium or zinc.

10. The preparation according to claim 1, and further comprising at least one water-soluble fluoride.

11. The preparation according to claim 10, wherein the at least one water-soluble fluoride is $NH_4F$, KF or NaF.

12. The preparation according to claim 10, wherein a content of the at least one water-soluble fluoride in the preparation is more than 0 to 10% by mass, based on a total mass of the preparation.

13. The preparation according to claim 10, wherein a content of the at least one water-soluble fluoride in the preparation is more than 0 to 5% by mass, based on a total mass of the preparation.

14. The preparation according to claim 1, and further comprising casein.

15. The preparation according to claim 14, wherein a content of the casein in the preparation is more than 0 to 30% by mass, based on a total mass of the preparation.

16. The preparation according to claim 14, wherein a content of the casein in the preparation is more than 0 to 15% by mass, based on a total mass of the preparation.

17. The preparation according to claim 14, wherein a content of the casein in the preparation is more than 0 to 5% by mass, based on a total mass of the preparation.

* * * * *